US012753060B1

(12) United States Patent
Orr

(10) Patent No.: US 12,753,060 B1
(45) Date of Patent: *Oct. 6, 2026

(54) ASEPTIC FILLING APPARATUS WITH FILTER

(71) Applicant: Timothy E. Orr, Redding, CA (US)

(72) Inventor: Timothy E. Orr, Redding, CA (US)

(73) Assignee: TORR INDUSTRIES, INC., Redding, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 18/389,145

(22) Filed: Nov. 13, 2023

(51) Int. Cl.

| | |
|---|---|
| ***A61J 1/20*** | (2006.01) |
| ***A61J 1/10*** | (2006.01) |
| ***A61J 1/14*** | (2023.01) |
| ***A61L 2/07*** | (2006.01) |
| ***A61L 2/08*** | (2006.01) |
| ***B67C 3/20*** | (2006.01) |
| ***B67C 3/26*** | (2006.01) |
| *B67C 3/22* | (2006.01) |

(52) U.S. Cl.
CPC .............. *B67C 3/2642* (2013.01); *A61L 2/07* (2013.01); *A61L 2/08* (2013.01); *B67C 3/20* (2013.01); *A61J 1/10* (2013.01); *A61J 1/14* (2013.01); *A61J 1/20* (2013.01); *B67C 2003/228* (2013.01)

(58) Field of Classification Search
CPC ... B67C 3/2642; B67C 3/20; B67C 2003/228; A61L 2/07; A61L 2/08; B65B 3/003; A61J 1/2048; A61J 1/1406; A61J 1/1443; A61J 1/1475; A61J 1/201; A61J 1/10; A61J 1/2024; A61J 1/2027; A61J 1/1431; A61J 1/1487
USPC .......................................................... 141/85
See application file for complete search history.

(56) References Cited

U.S. PATENT DOCUMENTS

| | | | | |
|---|---|---|---|---|
| 2,879,207 A * | 3/1959 | Poitras | C12M 23/10 | 435/287.7 |
| 3,527,029 A * | 9/1970 | Kirschner | A61M 5/162 | 604/405 |
| 4,035,304 A * | 7/1977 | Watanabe | A61M 5/165 | 210/317 |
| 4,276,170 A * | 6/1981 | Vaillancourt | B01D 36/001 | 96/6 |
| 4,805,378 A * | 2/1989 | Anderson | B65B 55/022 | 53/381.2 |
| 4,816,221 A * | 3/1989 | Harvey | A61L 2/07 | 422/26 |
| 5,224,937 A * | 7/1993 | van der Heiden | A61M 39/146 | 604/905 |
| 5,368,586 A * | 11/1994 | Van Der Heiden | A61J 1/2089 | 604/416 |
| 7,497,130 B2 * | 3/2009 | Woods | G01F 15/18 | 73/861.357 |

(Continued)

FOREIGN PATENT DOCUMENTS

| | | | | |
|---|---|---|---|---|
| CN | 216916386 U | 7/2022 | | |
| EP | 1935441 A1 * | 6/2008 | A61M 1/1694 | |
| NL | 2007929 C2 | 6/2013 | | |

*Primary Examiner* — Kenneth Rinehart
*Assistant Examiner* — Stephanie A Shrieves
(74) *Attorney, Agent, or Firm* — Theodore J. Bielen, Jr.

(57) ABSTRACT

An aseptic filling apparatus and method utilizing a filter, a flow meter, and a liquid passage unit allowing aseptic fluid to pass into a container. The filter and flow meter serve as a detector to indicate the integrity of the filter and the existence of contaminants in the aseptic fluid passed to the container.

9 Claims, 5 Drawing Sheets

(56) References Cited

U.S. PATENT DOCUMENTS

| | | | | |
|---|---|---|---|---|
| 11,478,406 | B1 * | 10/2022 | Rutter | A61J 1/1443 |
| 11,529,289 | B2 * | 12/2022 | Fangrow | A61J 1/201 |
| 11,622,912 | B2 * | 4/2023 | Rutter | A61J 1/1487<br>137/798 |
| 11,759,395 | B2 * | 9/2023 | Ding | A61J 1/10<br>604/406 |
| 12,326,442 | B2 * | 6/2025 | Samproni | B01L 3/5023 |
| 2003/0226857 | A1 * | 12/2003 | Bibbo | B01F 23/53<br>422/1 |
| 2004/0031744 | A1 * | 2/2004 | Nakashima | A61M 5/165<br>210/321.79 |
| 2006/0264897 | A1 * | 11/2006 | Lobl | A61P 27/16<br>604/117 |
| 2015/0290448 | A1 * | 10/2015 | Pavlik | A61J 1/201<br>604/533 |
| 2016/0374901 | A9 * | 12/2016 | Rodriguez | A61M 5/14276<br>141/2 |
| 2017/0203860 | A1 * | 7/2017 | Py | B65B 3/003 |
| 2018/0244510 | A1 * | 8/2018 | Harth | B67C 7/0086 |
| 2020/0222281 | A1 * | 7/2020 | Ding | A61J 1/2024 |
| 2020/0276085 | A1 * | 9/2020 | Linkner | A61K 38/4893 |
| 2021/0290486 | A1 * | 9/2021 | Ariagno | A61J 1/2055 |
| 2022/0133593 | A1 * | 5/2022 | Gobbi Frattini | A61J 1/2089<br>604/410 |

* cited by examiner

ASEPTIC FILLING APPARATUS WITH FILTER

BACKGROUND OF THE INVENTION

The present application relate to a novel and useful aseptic filling apparatus utilizing a filter that produces aseptic fluids of exceptional purity.

Aseptic processing of liquids involves the containerizing or packaging of sterile liquids in containers for later use.

For example, aseptic processing is used with liquid foods, such as milk, fruit juices, salad dressing, liquid eggs, and the like. Such aseptic processing is also employed to create medicinal liquids which may be human injectable liquids. The latter requires an extremely high degree of sterilization, commonly referred to as zero existence of microbes.

Sterilization refers to any process that removes, kills, or deactivates all forms of life, especially microorganisms such as fungi, bacteria, spores, unicellular eukaryotic organisms, prions, and the like. Sterilization can be achieved through various means, such as the application of heat, chemicals, irradiation, and high pressure. The degree of sterilization is commonly expressed by multiples of the decimal reduction time or D-value or log reduction. In any case, a high degree of sterilization is intended to achieve the destruction or complete removal of microorganisms.

In the past, conventional sterilization of aseptic liquids has been adequate for most food products. However, due to the presence of contaminates in fillers used with the processing of aseptic liquids, a very small degree of microorganisms are found in the final liquid. Needless of say, any degree of contamination by microorganisms in an aseptic liquid is not acceptable for use of such aseptic liquid in medicine and surgery applications.

Prior art processing of aseptic liquids has been recognized. For example, U.S. Pat. No. 4,805,378 describes an aseptic filling station which employs the filling of a container using a double membrane system.

United States Patent Publication 2020/0276085 describes a vial adaptor that mixes a diluent with a drug in a chamber where a vacuum is applied to the same. The combination of diluent and drug is then administered through a syringe. United States Patent Publication 2021/0290486 shows a female-female syringe adaptor that is used when reconstituting lyophilized powder.

United States Patent Application Publication 2022/0133593 describes a filter disposed between a bottle and a sterile bag that is used to compensate for pressure. Such diversion allows a bag being filled to communicated with a sealed side opening for a syringe.

China Patent to Liu et al., United States Patent Publication 2020/0222281, U.S. Pat. Nos. 11,759,395, 11,529,289, and Netherlands U.S. Pat. No. 2,007,929 show filters on inlets to sterile bags.

U.S. Pat. Nos. 11,478,406 and 11,622,912 describe aseptic filling apparatuses which use sterilization by radiation of the deliverable liquid.

An aseptic filling apparatus which creates a high degree of purity and provides feedback on the reliability of the filling method is needed in the field of medical products.

SUMMARY OF THE INVENTION

In accordance with the present application, a novel and useful filling apparatus and method for aseptic liquids is herein provided.

The apparatus and method of the present application comprises providing an adaptor having an entrance and exit that communicates with a tube leading to a container in the form of a bag. A pierceable membrane is sealed to the second end portion of the adaptor. Liquid flowing from a filler is measured by a flow meter prior to entering the adaptor.

Most importantly, a filter is placed within the passageway of the adaptor between the exit and entrance of the same. When membrane of the adaptor is pierced, aseptic liquid from the filler is passed through the flow meter, through the passageway of the adaptor, and through an opening in the tube leading to the container bag. The filter provides an extremely high degree of purity of the aseptic liquid, minimizing delivery of any microorganisms emanating from the filler feeding the container. In addition, the filter provides a certain degree of backpressure, which registers as a degree of flow of the aseptic liquid from the filler to the bag container. Excessive flow from the flow meter indicates a break or rupture of the filter and the absence of the filler's function. Filled bags, where the flow from the filler travels at a normal rate, are accepted, or passed, as containing aseptic liquid of a very high degree of purity. On the other hand, bags filled when the flow meter indicates an excessive flow are rejected.

The passed or accepted filled bags may then be isolated as a unit by severing the tube leading to the bag for later use. The adaptor containing the filter is then discarded.

It may be apparent that a novel and useful method and apparatus for filling aseptic liquids has been hereinabove described. It is therefore an object of the present application to provide a method and apparatus for filling aseptic liquids which further sterilize the aseptic liquid from a filler by the use of a filter located in a portion of the apparatus.

Another object of the present application is to provide a method and apparatus for transporting aseptic liquid from a filler that includes a detection mechanism that indicates the status of the filter within the apparatus prior to the aseptic liquid filling a container such as a bag.

Another object of the present application is to provide a method and apparatus for transporting aseptic liquid from a filler that provides the user with an indication of the integrity of the filter with the apparatus during the filling process.

Another object of the present application is to provide a method and apparatus for transporting aseptic liquid from a liquid filler that produces aseptic liquid having a high degree of purity, free of microorganisms, which is an aseptic liquid that may be usable for medical or surgical purposes.

Yet another object of the present application is to provide a method of transporting an aseptic liquid from a liquid filler that results in a unit containing microorganism-free liquid, which may be stored for later use.

The application possesses other objects and advantages especially as concerns particular characteristics and features thereof which will become apparent as the specification continues.

For a better understanding of the application, reference is made to the following detailed description of the preferred embodiments thereof, which should be referenced to the prior described drawings.

DETAILED DESCRIPTION OF THE PREFERRED EMBODIMENTS

Various aspects will evolve from the following detailed description of the preferred embodiments, which should be taken in conjunction with the prior delineated drawings.

Figure 1:
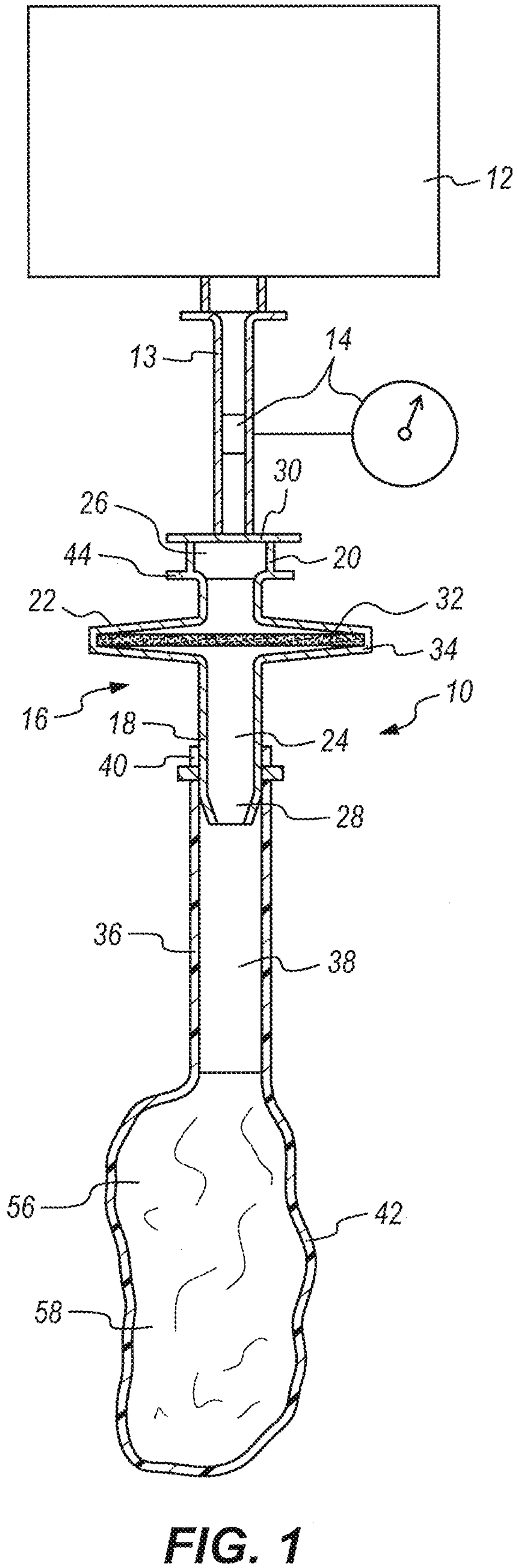
FIG. 1 is a sectional view of the apparatus of the present application.

The aseptic filling apparatus as a whole is indicated by reference character 10. Apparatus 10, FIG. 1, is used in conjunction with a filler 12, shown schematically in FIG. 1. Filler 12 may be of the type normally used to deliver aseptic fluid to a container for use. For example, filler 12 may take the form of a Torr Filler 170 manufactured by Torr Industries, Inc. of Redding, California. Aseptic liquid being delivered by filler 12 may be of high quality suitable for foodstuffs, such as milk, fruit juices, salad dressing, ice cream mix, and the like. However, such fluids may not be suitable for surgical instruments and medications, the latter of which are human injectable. Although the aseptic liquid delivered 12 may be sterile, contaminants of microorganisms found within filler 12 often create a filler output of liquid that possesses a minute concentration of microorganism. Such a liquid is unsuitable for medical and surgical purposes.

Aseptic liquid exiting filler 12 passes through conduit 13 and through a flow meter 14. Flow meter 14 indicates the rate of delivery of aseptic liquid from filler 12. After passing through flow meter 14, aseptic liquid is the transferred into an adaptor 16, shown in the drawings as a cylindrical body. Adaptor 16 has a first end portion 18, a second end portion 20, and an intermediate portion 22. Further, adaptor 12 possess a passageway 24 which receives aseptic liquid from filler 12 and flow meter 14 through entrance 26 and exit 28. A permeable membrane lies adjacent entrance 26 to passageway 24 of adaptor 16. A filter 32 is positioned within intermediate portion 22 of adaptor 16. Specifically, filter 32 lies in an enlarged section 34 of intermediate portion 22 and is intended to screen the entire flow entering adaptor 16 from filter 12 and flow meter 14.

Again referring to FIGS. 1 and 2, it may be observed that a tube 36 is employed in the present apparatus 10. Tube 36 includes an opening or aperture 38. Tube 36 is held to first end portion 18 of adaptor 16 by a tie 40. Thus, passageway 24 of adaptor 16 communicates with aperture 38 of tube 36. Tube 36 leads to a container 42, shown as a polymeric bag. Container 42 may vary in size depending on the desired capacity of the same. A flange 44 of adaptor 16 aids in the connection of the same to filling apparatus 12. Also, adaptor 16 includes a barbed end 46 to aid in the connection of adaptor 16 to tube 36.

Figure 2:
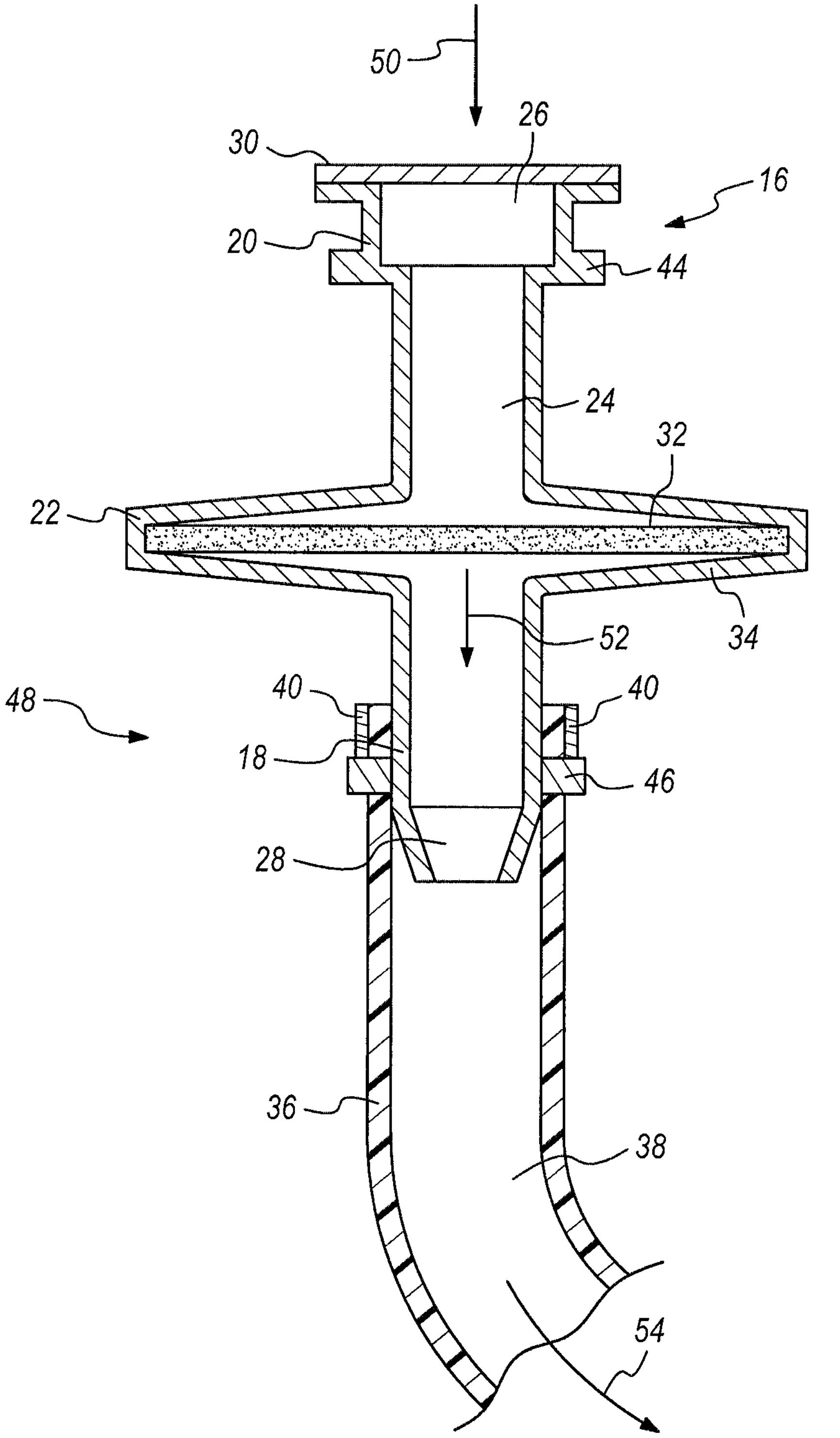
FIG. 2 is a sectional view of the adaptor portion of the apparatus of the present application showing an internal filter.

Adaptor 16, tube 36, and container 42 are formed into a unit 48 that is sterilized by any suitable means, such as irradiation, steam, pressure, and the like. FIG. 2 shows the general movement of aseptic liquid 50 from filler 12 through unit 48 represent by directional arrows 50, 52, and 54. Container 42 is depicted as being filled with aseptic liquid 56 on FIG. 1.

Figure 3:
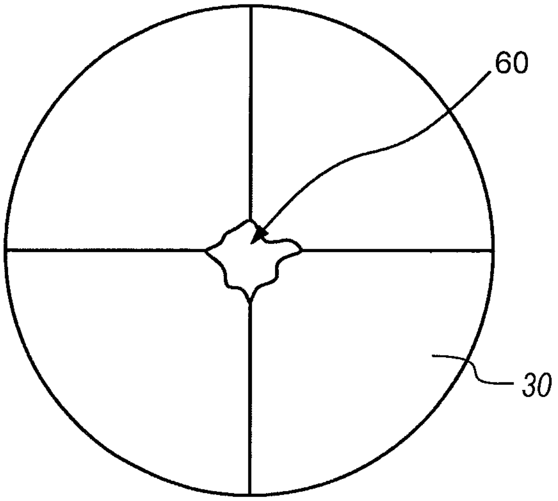
FIG. 3 is a schematic end view of the apparatus depicted in FIGS. 1 and 2 indicating the puncturing of a membrane.
Figure 4:
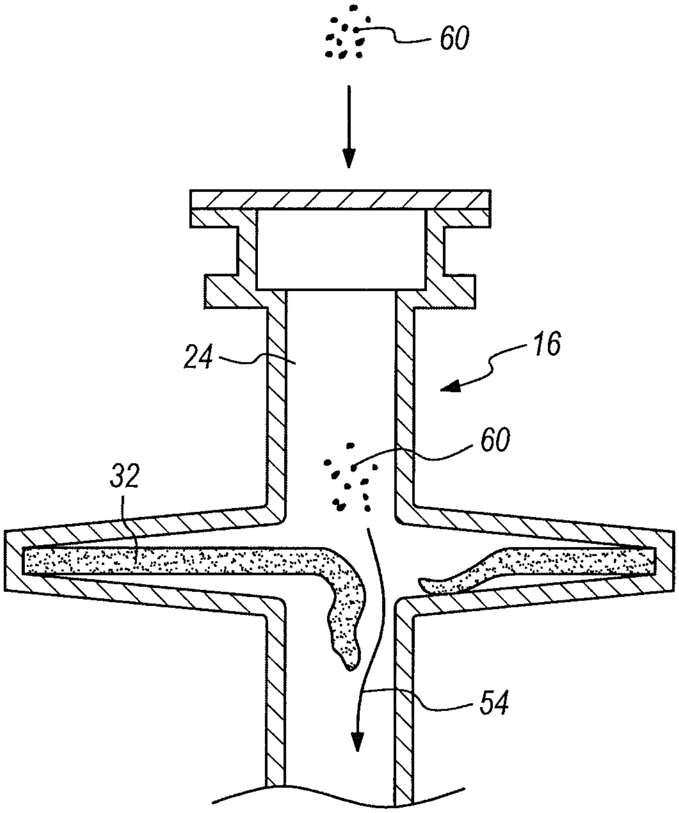
FIG. 4 is a partial sectional view of the adaptor portion of the present application showing the rupture of the filter within the adaptor.

Apparatus 10 operates by filler 12 passing aseptic liquid through flow meter 14 and to adaptor 16, once membrane 30 has been pierced as illustrated schematically in FIG. 3. Such piercing may be integral to the operation of filler 12. That is to say, aseptic liquid, after passing through flow meter 14, enters passageway 24 of adaptor 16, travels through filter 32 to opening 38 of tube 36, and then further moves into a chamber 58 of bag or container 42. Again, although the liquid exiting filler 12 is generally described as being aseptic, microbial contaminants within filler 12 may enter aseptic liquid from filler 12 before entering chamber 58 of container 42. However, filter 32 removes any stray microbial contaminants in aseptic liquid exiting filler 12 and flow meter 14.

Figure 5:
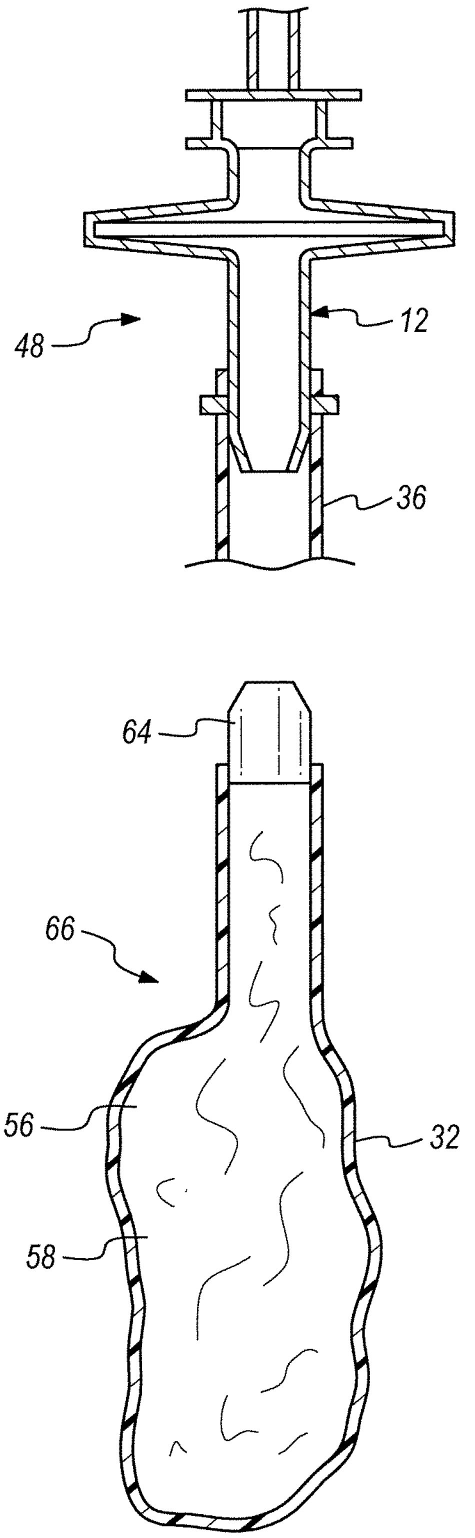
FIG. 5 is a sectional view of the apparatus of the present application showing the severing of the filled container from the discardable portion of the apparatus.
Figure 6:
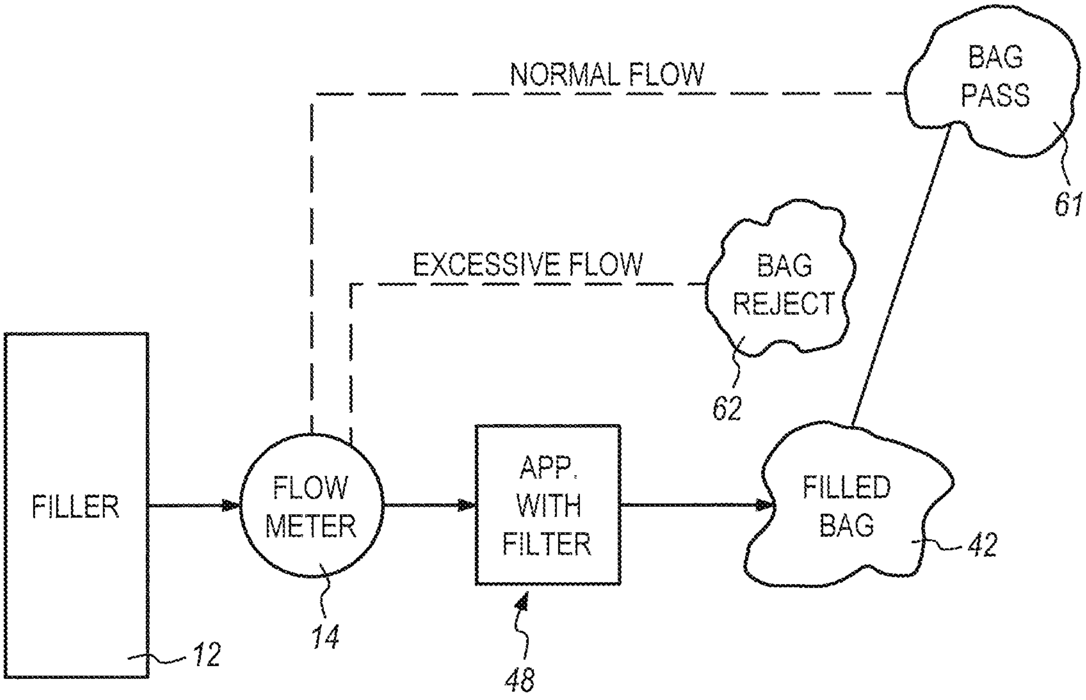
FIG. 6 is a block diagram showing the overall method of producing a microorganism-free aseptic liquid using the apparatus of the present application shown in FIGS. 1, 2, and 3.

In addition, filter 32 acts as a source of backpressure and serves as a detector of the status of filter 32. Such backpressure provided by filter 32 causes flow meter 14 to read a certain flow rate into container bag 42. However, if filter 32 is ruptured, the flow rate measured by flow meter 14 will markedly increase. FIG. 3 illustrates a ruptured filter 32 during the flow of aseptic liquid 54 through passageway 24. At this point, stray microbes or microbial contaminants 60 are able to pass through passageway 24 of adaptor 16 entering container bag 42. Needless to say, the contents of container bag 42 through a ruptured filter 32 will result in container 42 having an unacceptable amount of microbial contaminants for medical or surgical use. With reference to FIG. 5, a block diagram is shown outlining the process of the present application. Specifically, when flow meter 14 detects a normal flow, bag 42 is considered a "bag pass" 61 and is usable for medical and surgical purposes. On the other hand, should flow meter 14 detect excessive flow, bag 42 would be categorized as a "bag reject" 62 and is discarded.

Once container 32 is filled with a purified aseptic liquid 56, adaptor 12 of unit 48 is severed by cutting tube 36. Unit 48 is the discarded. Container 32, filled with acceptable aseptic fluid, is then sealed with a plug or otherwise forming a source of aseptic fluid unit 66 which may be stored or transported for use at a later time. The user would remove plug 64 and empty the contents from chamber 58 of bag 32 as needed.

While in the foregoing, embodiments of the application have been set forth in considerable detail for the purposes of making a complete disclosure of the application, it may be apparent to those of skill in the art that numerous changes may be made in such details without departing from the spirit and principles of the application.

What is claimed is:

1. A method of transporting an aseptic liquid from a liquid filler, comprising the steps of:
- providing an adaptor comprising a first end portion, a second end portion, and an intermediate portion, said adaptor further comprising an aseptic liquid passageway therethrough, said passageway further comprising an exit from said passageway at said first end portion and an entrance to said passageway at said second end portion;
- positioning a pierceable membrane to seal second end portion of said adaptor;
- placing a sterile filter in said passageway of said adaptor between said exit and said entrance of said passageway to remove microbial contaminants from the aseptic liquid in said aseptic liquid passageway and further to provide a back pressure source;

providing a flow meter to measure the flow state of aseptic liquid from the liquid filler to said entrance of said adaptor;

providing a severable tube having an opening therethrough;

providing a container possessing a chamber;

holding and leading said tube to said first end portion of said adaptor and to said container, permitting communication of said opening through said tube with said chamber of said container and said passageway of said adaptor;

attaching said second end portion of said adaptor to the liquid filler;

piercing said membrane;

passing aseptic liquid from the liquid filler through said pierced membrane, through said aseptic liquid passageway of said adaptor, through said filter, through said tube opening, and to said chamber of said container; and determining the flow rate of the aseptic liquid passed from the liquid filler measured by said flow meter, from said back pressure provided by said filter; and assessing excessive flow of aseptic liquid from said flow meter and rejecting the usability for medical and surgical purposes of the aseptic liquid passed to the chamber of said container.

2. The method of claim 1, which additionally comprises sterilizing said adaptor, said tube, and said container prior to said step attaching said second end portion of said adaptor to the liquid filer.

3. The method of claim 2, in which said step of sterilizing said adaptor, said tube, and said container comprises sterilizing by the use of radiation.

4. The method of claim 2, in which said step of sterilizing said adaptor, said tube, and said container comprises sterilizing by the use of steam.

5. The method of claim 1, which additionally comprises the step of severing and sealing said tube.

6. The method of claim 5, which further comprising sterilizing said adaptor, said container and said severable tube prior to said step of severing and sealing said tube.

7. The method of claim 1 in which said adaptor comprises a cylindrical body.

8. The method of claim 1, in which said container comprises a polymeric bag.

9. The method of claim 1, in which said adaptor further comprises a barbed configuration at said first end.

* * * * *